(12) United States Patent
Reimer et al.

(10) Patent No.: US 7,889,423 B2
(45) Date of Patent: Feb. 15, 2011

(54) SURGICAL MICROSCOPE HAVING AN OCT-SYSTEM AND A SURGICAL MICROSCOPE ILLUMINATING MODULE HAVING AN OCT-SYSTEM

(75) Inventors: Peter Reimer, Ellwangen (DE); Christoph Hauger, Aalen (DE); Alfons Abele, Schwäbisch Gmünd (DE); Markus Seesselberg, Aalen (DE)

(73) Assignee: Carl Zeiss Surgical GmbH, Oberkochen (DE)

( * ) Notice: Subject to any disclaimer, the term of this patent is extended or adjusted under 35 U.S.C. 154(b) by 367 days.

(21) Appl. No.: 11/984,817

(22) Filed: Nov. 21, 2007

(65) Prior Publication Data
US 2008/0117503 A1 May 22, 2008

(30) Foreign Application Priority Data
Nov. 6, 2006 (DE) .................. 10 2006 052 513
Apr. 24, 2007 (DE) .................. 10 2007 019 677

(51) Int. Cl.
*G02B 21/00* (2006.01)
(52) U.S. Cl. ................. 359/368; 359/385; 359/390
(58) Field of Classification Search .......... 359/368–390
See application file for complete search history.

(56) References Cited

U.S. PATENT DOCUMENTS

| | | | |
|---|---|---|---|
| 5,321,501 A | 6/1994 | Swanson et al. | |
| 5,535,052 A * | 7/1996 | Jorgens | 359/388 |
| 5,748,367 A * | 5/1998 | Lucke et al. | 359/385 |
| 5,795,295 A | 8/1998 | Hellmuth et al. | |
| 6,095,648 A | 8/2000 | Birngruber et al. | |
| 6,741,359 B2 * | 5/2004 | Wei et al. | 356/512 |
| 6,862,137 B2 * | 3/2005 | Ott | 359/388 |

FOREIGN PATENT DOCUMENTS

| | | |
|---|---|---|
| DE | 10 2004 049 368 | 4/2006 |
| WO | WO 03/070090 | 8/2003 |
| WO | WO 2006/100544 | 9/2006 |

OTHER PUBLICATIONS

Expanded Search Report of the EPO.

* cited by examiner

*Primary Examiner*—Thong Nguyen
(74) *Attorney, Agent, or Firm*—Walter Ottesen

(57) ABSTRACT

A surgical microscope (100) has an illuminating module (120). The illuminating module contains an illuminating optic which images a field diaphragm (124) to a parallel illuminating beam path at infinity. The field diaphragm (124) is illuminated by a light source. The illuminating optic includes a first lens assembly and a second lens assembly which functions to image the field diaphragm (124) into the object region (108) via the microscope main objective (101) of the surgical microscope (100). An in-coupling element (128) is provided between the first lens assembly (125) and the second lens assembly (126) and this in-coupling element couples the OCT-scanning beam into the illuminating beam.

23 Claims, 4 Drawing Sheets

SURGICAL MICROSCOPE HAVING AN OCT-SYSTEM AND A SURGICAL MICROSCOPE ILLUMINATING MODULE HAVING AN OCT-SYSTEM

CROSS REFERENCE TO RELATED APPLICATION

This application claims priority of German patent application no. 10 2007 019 677.8, filed Apr. 24, 2007, the entire content of which is incorporated herein by reference.

FIELD OF THE INVENTION

The invention relates to a surgical microscope having a viewing beam path for examining a region of an object. The surgical microscope includes an illuminating system having an illuminating optic which images a field diaphragm illuminated by a light source to a parallel illuminating beam at infinity. The illuminating optic includes a first lens assembly and a second lens assembly and the surgical microscope includes an objective which is mounted in the parallel illuminating beam path in order to image the field diaphragm onto the object region. The surgical microscope also includes an OCT-system for examining the object region and the OCT-system includes an OCT-scanning beam which is conducted through the objective.

The invention further relates to a surgical microscope illuminating module for connection to a surgical microscope having a receptacle for a first light conductor in order to provide the illuminating light. The illuminating module includes a field diaphragm which can be illuminated with light from the light conductor and an illuminating optic which can image the field diaphragm to a parallel imaging beam at infinity. The illuminating optic includes a first lens assembly and a second lens assembly and an illuminating mirror which functions to direct the illuminating light, which exits from the field diaphragm, with a parallel imaging beam through the microscope main objective to the object region.

BACKGROUND OF THE INVENTION

A surgical microscope of the kind described above is known from U.S. Pat. No. 5,795,295. This surgical microscope includes an OCT-system (optical coherence tomography) which generates an OCT-scanning beam from laser beam radiation. The OCT-system includes an analyzing unit for evaluating interference signals. The OCT-system includes a device for scanning the OCT-scanning beam and two scan mirrors which can be displaced about two axes of movement. The OCT-scanning beam in the surgical microscope is coupled into the illuminating beam path of the surgical microscope via a divider mirror. The OCT-scanning beam and the illuminating beam are deflected through the microscope main objective to the object region.

The Carl Zeiss Surgical Microscope System OPMI® Visu 200 includes a surgical microscope illuminating module of the kind described above. This illuminating module is configured for attachment to the base body of a surgical microscope. The illuminating module includes an illuminating optic in the form of two lens assemblies which transpose an illuminated field diaphragm into a parallel imaging beam path which runs perpendicularly to the optical axis of the microscope main objective when the illuminating module is connected to the surgical microscope. The field diaphragm is illuminated with light from the light conductor. The illuminating module contains two illuminating mirrors which deflect the illuminating light parallel to the optical axis of the microscope main objective.

An OCT-system (Optical Coherence Tomography) permits the non-invasive illustration and measurement of structures within a tissue utilizing optical coherence tomography. As an image providing process, the optical coherence tomography permits especially section images or volume images of biological tissue to be generated with micrometer resolution. A corresponding OCT-system includes a source for time-dependent incoherent and spatially coherent light having a specific coherence length which is guided to a specimen beam path and a reference beam path. The specimen beam path is directed onto the tissue to be examined. Laser radiation, which is radiated back into the specimen beam path because of scatter centers in the tissue, superposes the OCT-system with laser radiation from the reference beam path. An interference signal results because of the superposition. The position of scatter centers for the laser radiation in the examined tissue can be determined from this interference signal.

For OCT-systems, the building principles of the "time-domain OCT" and of the "Fourier-domain OCT" are known.

The configuration of a "time-domain OCT" is described, for example, in U.S. Pat. No. 5,321,501 with reference to FIG. 1a at column 5, line 40, to column 11, line 10. In a system of this kind, the optical path length of the reference beam path is continuously varied via a rapidly moving reference mirror. The light from specimen beam path and reference beam path is superposed on a photo detector. When the optical path lengths of the specimen and reference beam paths are coincident, then an interference signal is provided on the photo detector.

A "Fourier-domain OCT" is, for example, described in international patent publication WO 2006/100544 A1. To measure the optical path length of a specimen beam path, light from a reference beam path is superposed onto light from a specimen beam path. In contrast to the time-domain OCT, the light from the specimen beam path and reference beam path is not supplied directly to a detector for a measurement of the optical path length of the specimen beam path but is first spectrally dispersed by means of a spectrometer. The spectral intensity of the superposed signal generated in this manner from specimen beam path and reference beam path is then detected by a detector. By evaluating the detector signal, the optical path length of the specimen beam path can be determined.

SUMMARY OF THE INVENTION

It is an object of the invention to provide a surgical microscope having an OCT-system which can fit structurally into a low volume and whose assembly principle permits a simple retrofitting of surgical microscopes for OCT. It is also an object of the invention to provide a surgical microscope illuminating module having an integrated OCT-system for connecting to a surgical microscope.

The surgical microscope of the invention is for defining a viewing beam path for examining an object region. The surgical microscope comprises: an illuminating system defining an illuminating beam path and including a light source for generating an illuminating light; the illuminating system further including a field diaphragm arranged in the illuminating beam path and being illuminated by the illuminating light; the illuminating system further including an illuminating optic arranged in the illuminating beam path downstream of the field diaphragm for imaging the field diaphragm at infinity with an illuminating beam having parallel rays; the illuminating optic including first and second lens assemblies arranged in the illuminating beam path; an objective arranged in the illuminating beam path for imaging the parallel rays of the field diaphragm onto the object region; an OCT-system for examining the object region; the OCT-system providing an OCT-scanning beam guided through the objective; and, an in-coupling element disposed in the illuminating beam path between the first and second lens assemblies for coupling the OCT-scanning beam into the illuminating beam path.

The illuminating module of the invention is for attachment to a surgical microscope defining a viewing beam path for examining an object region and the surgical microscope has a microscope main objective for passing the viewing beam to the object region. The illuminating module comprises: an illuminating system defining an illuminating beam path; a first receptacle for accommodating a first light conductor for providing illuminating light; the illuminating system further including: a field diaphragm arranged in the illuminating beam path and being illuminated by the illuminating light; and, an illuminating optic disposed in the illuminating beam path downstream of the field diaphragm for imaging the field diaphragm at infinity with an illuminating beam having parallel rays; the illuminating optic including first and second lens assemblies arranged in the illuminating beam path; an illuminating mirror disposed along the illuminating beam path downstream of the field diaphragm for directing the illuminating light exiting from the field diaphragm with parallel imaging rays through the microscope main objective to the object region; a second receptacle for accommodating a second light conductor for providing an OCT-scanning beam of an OCT-system; and, an in-coupling element disposed in the illuminating beam path between the first and second lens assemblies for coupling the OCT-scanning beam into the illuminating beam path.

According to another feature of the invention, the in-coupling element in the surgical microscope or surgical microscope illuminating module is configured as a divider mirror especially in the form of a planar mirror or a divider cube.

According to another feature of the invention, in the surgical microscope, the objective, which is mounted in the parallel illuminating beam path, is configured as a microscope main objective and the viewing beam of the surgical microscope passes through this microscope main objective. In this way, an especially compact structural configuration of the surgical microscope is achieved.

According to another feature of the surgical microscope of the invention, a path-folding device for the illuminating light is provided on the side of the objective facing away from the object. This path-folding device deflects the illuminating light of the illuminating device to the objective. In this way, an illumination is possible which is axis-near to the viewing beam paths and this can be of advantage for ophthalmologic surgical procedures.

According to another feature of the invention, the path-folding device is configured as a beam divider through which the viewing beam path of the surgical microscope passes. In this way, illuminating light can be guided in the viewing beam paths of the surgical microscope to the object region.

According to another feature of the invention, the surgical microscope includes an OCT-system for scanning the OCT-scanning beam with a first scan mirror. Preferably, a second scan mirror is provided. The first scan mirror can be moved about a first rotational axis and the second scan mirror can be moved about a second rotational axis. The first rotational axis and the second rotational axis are offset laterally at right angles to each other. In this way, a scanning of the object region is possible with a perpendicularly running raster pattern.

According to another feature of the invention, the surgical microscope includes an OCT-system having a light conductor which has a light exit section for the OCT-scanning beam. This light exit section is held so as to be movable. In this way, an OCT-scanning plane can be varied in the object region and it is possible to adjust the system for different OCT-wavelengths in view of the optical components in the viewing beam path. These optical components are designed for visible light.

According to another feature of the invention, the surgical microscope includes an OCT-system having a displaceable collimating optic which transposes the OCT-scanning beam into an essentially parallel scanning beam with the second lens assembly of the illuminating optic. In this way, it is possible to shift the OCT-scanning plane in the surgical microscope relative to the viewing plane of the optical viewing beam paths of the system.

Preferably, the surgical microscope illuminating module includes a unit for scanning the OCT-scanning beam. This unit for scanning can, for example, include a first scan mirror and a second scan mirror. An object region can be scanned with a perpendicularly running raster pattern in that the first scan mirror is moved about a first rotational axis and the second scan mirror is moved about a second rotational axis. The first rotational axis and the second rotational axis are laterally offset at right angles to each other.

According to another feature of the invention, the light exit section of the light conductor for the OCT-scanning beam is movably held in the surgical microscope illuminating module so that the OCT-scanning plane can be adjusted.

It is possible to shift the OCT-scanning plane of the OCT-system relative to a viewing plane for optical viewing beam paths in that an adjustable collimating optic is provided in the surgical microscope illuminating module by means of which the OCT-scanning beam is transposed into an essentially parallel scanning beam with the second lens assembly of the illuminating optic.

BRIEF DESCRIPTION OF THE DRAWINGS

The invention will now be described with reference to the drawings wherein.

DESCRIPTION OF THE PREFERRED EMBODIMENTS OF THE INVENTION

Figure 1:
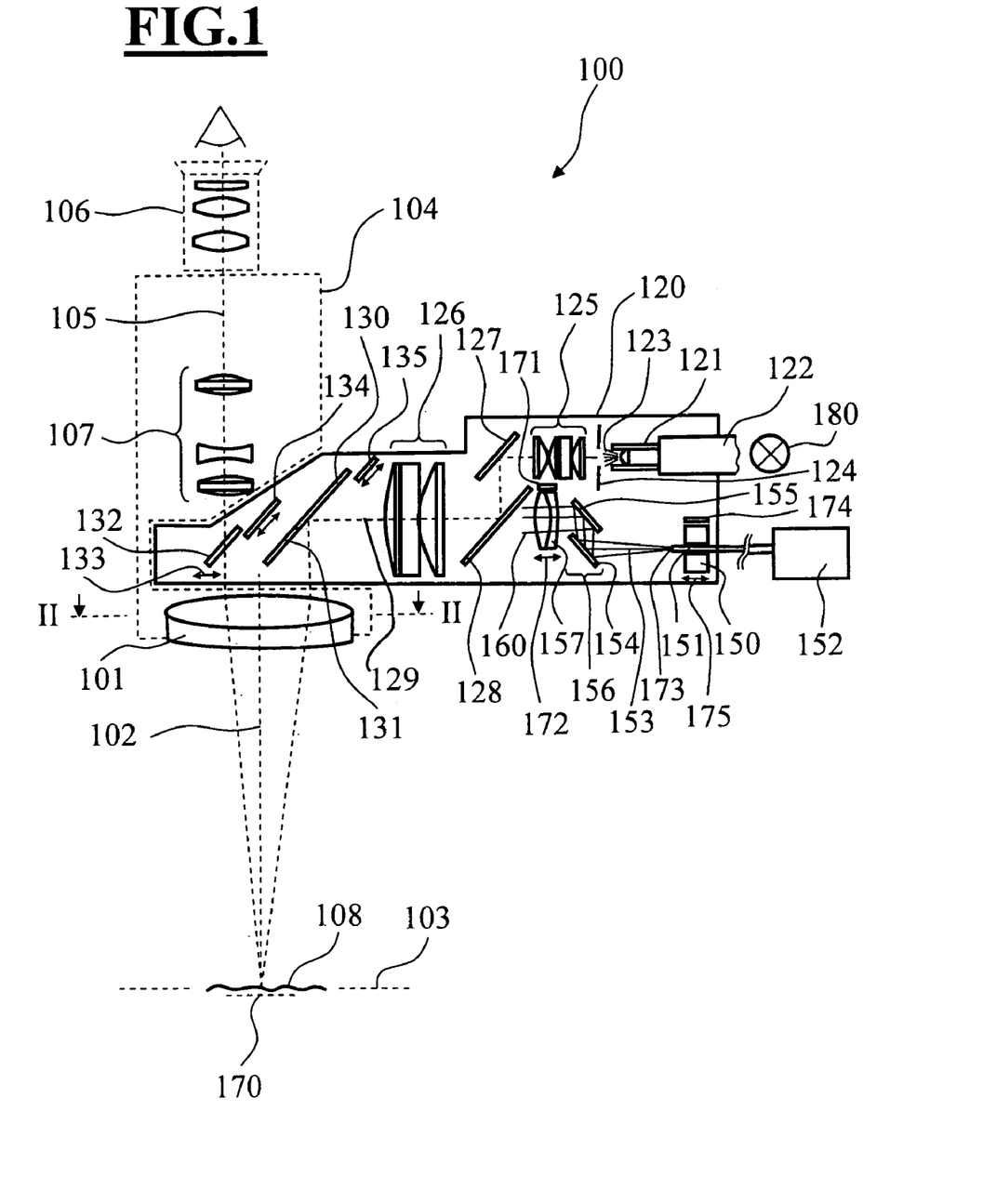
FIG. 1 is a schematic of a surgical microscope having an illuminating module wherein an OCT-system is integrated.

The surgical microscope 100 in FIG. 1 has a microscope main objective 101 defining an optical axis 102 as well as a focus plane 103. The microscope main objective 101 is accommodated in a surgical microscope base body 104. Stereoscopic viewing beam paths of a binocular tube 106 are represented by broken line 105 in FIG. 1 and pass through the microscope main objective 101. The surgical microscope 100 includes a zoomable magnification system 107.

The surgical microscope 100 has an illuminating unit in the form of an illuminating module 120 for illuminating the object region 108. This illuminating module 120 includes a receptacle 121 for a first light conductor 122 which provides illuminating light 123 from a light source (180). An adjustable field diaphragm 124 is illuminated with an illuminating light 123 exiting from the first light conductor 122. An illuminating optic is mounted in the illuminating module 120. The illuminating optic includes the following: a first lens assembly 125; a second lens assembly 126; and, four mirrors (127, 128, 130, 132).

The mirror 127 deflects the illuminating light, which exits from the first lens assembly 125, to the mirror 128 from where it reaches the second lens assembly 126. The first lens assembly 125 and the second lens assembly 126 image the field diaphragm 124 at infinity. In this way, illuminating light 123 having a parallel beam path exits from the second lens assembly 126. At the exit end of the second lens assembly 126, the optical axis 129 of the illuminating beam path runs perpendicularly to the optical axis 102 of the microscope main objective 101. The illuminating beam is guided onto an illuminating mirror 130 which has a breakthrough 131. The illuminating mirror 130 deflects the illuminating light parallel to the optical axis 102 of the microscope main objective 101 to the object region 108.

The illuminating module 120 further includes an illuminating mirror 132 to which illuminating light is guided which passes through the breakthrough 131 in the illuminating mirror 130.

The illuminating mirror 132 can be shifted perpendicularly to the optical axis 102 of the microscope main objective 101 in correspondence to the double arrow 133. This makes it possible to adjust the angle of incidence for the illuminating light in the object region 108.

Adjustable diaphragms (134, 135) are assigned to the illuminating mirrors (130, 132), respectively, to vary the intensity of the illuminating light guided to the object region. By adjusting the diaphragms (134, 135), the intensity of the illuminating light can be varied which is guided through the microscope main objective 101.

The illuminating module 120 includes a receptacle 150 for a second light conductor 151 which is connected to an OCT-system 152.

The OCT-system 152 makes possible the recordation of OCT-images for examining the object region 108. The OCT-system 152 includes a unit for generating and analyzing an OCT-scanning beam 153.

The OCT-system 152 is preferably integrated into a stand console (not shown) of the surgical microscope. Basically, the OCT-system can be accommodated also in the illuminating module 120.

The scanning beam 153, which exits from the second light conductor 151, is guided to a first scan mirror 154 and a second mirror 155 of an OCT-scan unit 156. The scanning beam 153 passes through a converging lens 157 downstream of the OCT-scan unit 156.

The beam 160 from the OCT-scan unit 156 is guided to the mirror 128. The mirror 128 acts as a divider mirror. This mirror reflects the illuminating light, which exits from the first light conductor 122, almost completely but is transparent for the OCT-scanning beam. In this way, the OCT-scanning beam 153 is superposed on the illuminating light 123. In the module 120, the mirror 128 is configured as a planar plate. The mirror 128 could also, however, be configured as a divider cube.

The light of the OCT-scanning beam 153 is guided via the illuminating mirrors (130, 132) with the illuminating light to the object region 108. The OCT-scanning beam 153 is bundled in an OCT-scanning plane 170 with the following: the converging lens 157; the second lens assembly 126 of the illuminating optic in the illuminating module 120; and, the microscope main objective 101. The OCT-scanning plane 170 is the plane of the geometric image of the front face 173 of the second light conductor 151 in the object region 108. The geometric image of the front face 173 is determined by the following optical elements in the OCT-scanning beam path: OCT-scan unit 156; converging lens 157; mirror 128; mirror 130; mirror 132; and, microscope main objective 101. More specifically, the corresponding geometric image of the light conductor front face 173 lies in the OCT-scanning plane 170. To adjust the OCT-scanning plane, on the one hand, the converging lens 157 is held so as to be movable in correspondence to the double arrow 172 via a position drive 171. On the other hand, the front face 173 of the second light conductor 151 for the OCT-scanning beam can be shifted in correspondence to the double arrow 175 by a positioning device 174. The reference beam in the OCT-system is readjusted as far as needed when the OCT-scanning plane 170 is adjusted.

The light, which is backscattered into the OCT-scanning beam path, arrives back in the OCT-system 152 via the following: the microscope main objective 101; the mirrors (132, 130); the lens assembly 126 and the mirror element 128. There, the OCT-scanning light, which is backscattered from the object region, interferes with the OCT-beam from a reference beam path. The interference signal is detected by a detector and is evaluated by a computer unit which, from this signal, determines an optical path length difference between scatter centers for OCT-light in the object region and the path length of light in the reference branch.

Figure 2:
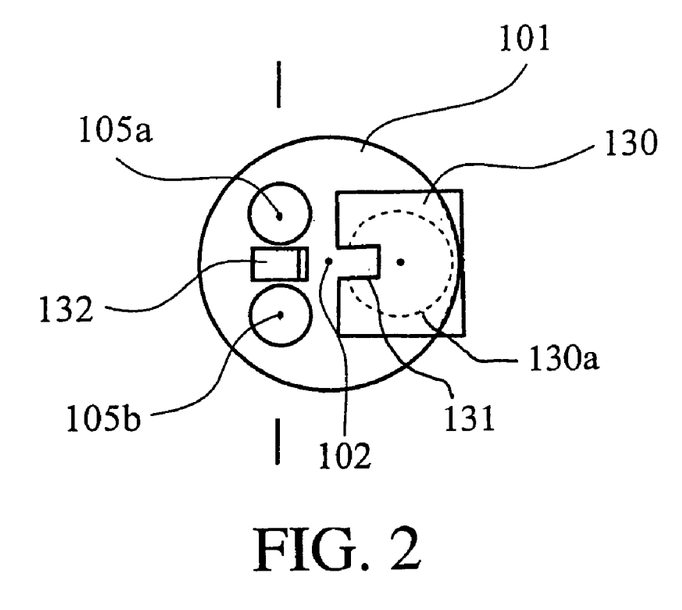
FIG. 2 is a section view of the microscope main objective taken along line II-II of FIG. 1.

FIG. 2 is a section view taken along line II-II of FIG. 1 and shows the illuminating mirrors (130, 132) and shows the course of the stereoscopic viewing beam paths (105a, 105b) in the surgical microscope 100 of FIG. 1. Two stereoscopic component beams (105a, 105b) pass through the microscope main objective 101. The optical axis 102 of the microscope main objective 101 lies at the center thereof. The circular broken line 130a indicates the beam deflected by mirror 130.

Figure 3:
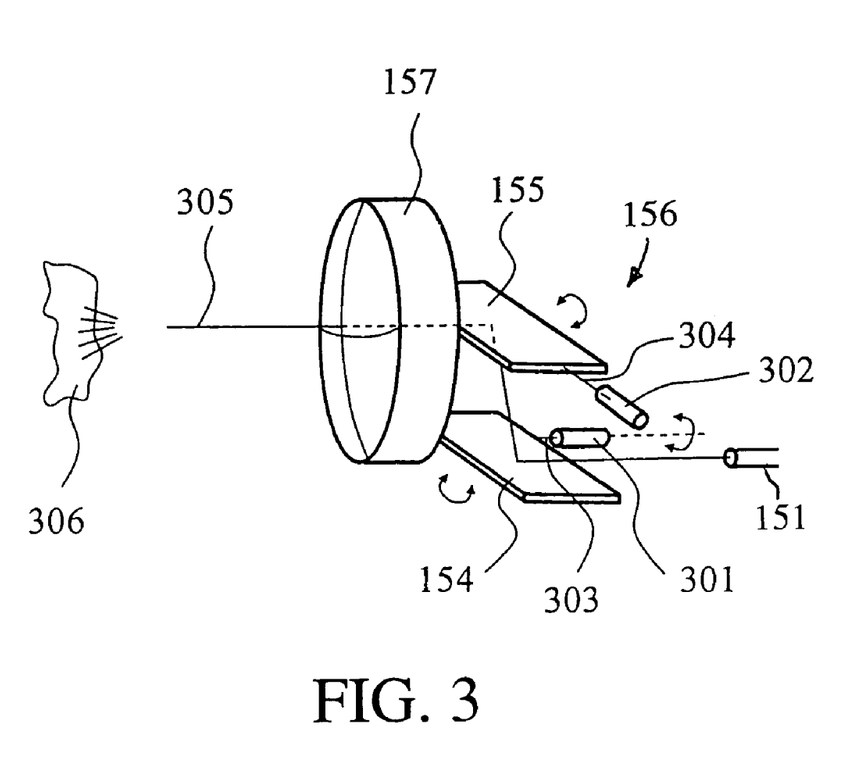
FIG. 3 is a perspective detail view of the illuminating module with the OCT-system.

FIG. 3 shows the OCT-scan unit 156 of the surgical microscope 100 of FIG. 1. The first scan mirror 154 and the second scan mirror 155 are arranged to be rotatably movable via positioning drives (301, 302) about two mutually perpendicular axes (303, 304). This permits the OCT-scanning beam path 305 to scan over a plane 306.

Figure 4:
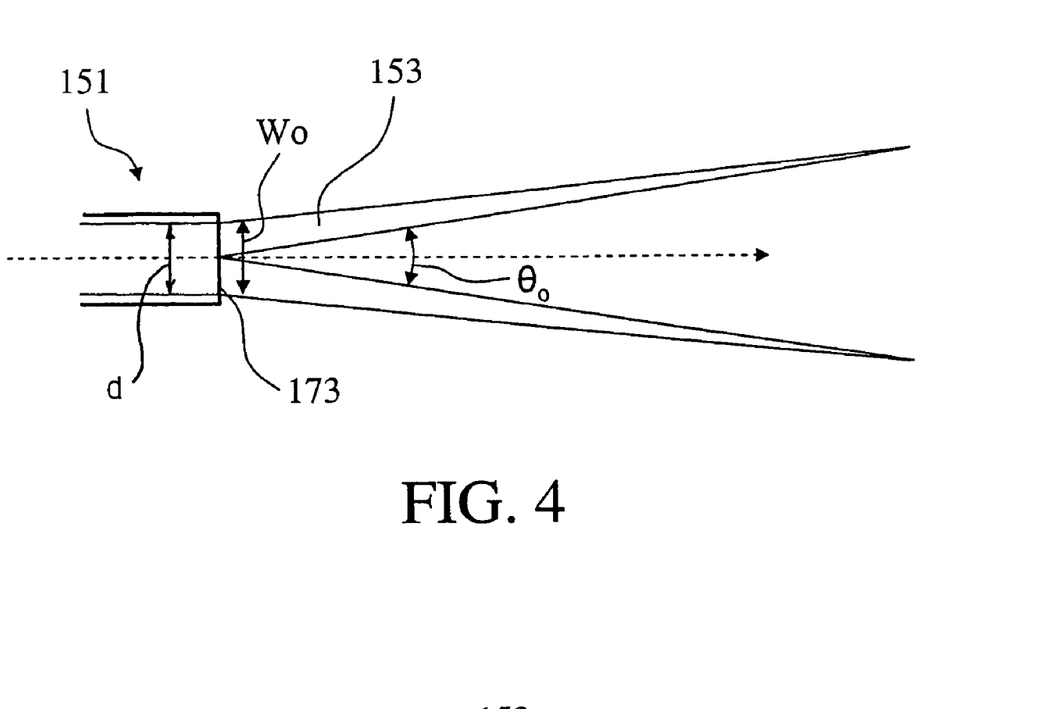
FIG. 4 shows an intensity distribution of the OCT-scanning light beam exiting from the light conductor of the OCT-system in the surgical microscope.

FIG. 4 shows the front portion of the second light conductor 151 of FIG. 1 having front face 173. The light conductor 151 operates as a monomode fiber for light of the wavelength $\lambda=1310$ nm. The diameter (d) of the fiber core of the light conductor 151 satisfies the relationship:

$$\frac{d}{2} < 2.4 \frac{\lambda}{2\pi NA},$$

wherein: NA is the numerical aperture of the front face of the light conductor. Preferably, the diameter (d) of the fiber core of the light conductor 151 lies in the range of 5 µm<d<10 µm. In this parameter range, the light conductor 151 conducts the light with a Gaussian-shaped wave mode. The OCT-scanning light beam 153 exits from the light conductor 151 with an approximately Gaussian-shaped beam profile which is characterized by a waist parameter $W_0$ and an aperture parameter $\theta_0$ wherein:

$$\theta_0 = \frac{2\lambda}{\pi W_0}$$

An aperture angle of $\theta_0 \approx 0.0827$ rad results thereby as an index for the beam divergence for a fiber core diameter of $d_0=10$ µm and a wavelength $\lambda_0=1310$ nm.

The front face 173 of the second light conductor 151 is imaged by the microscope main objective 101 onto the object region 108 in the OCT-scanning plane 170 via the following: the scan mirrors 154 and 155 in the surgical microscope 100 of FIG. 1; the converging lens 157; the mirror 128; the second lens assembly 126; the mirror 130; and, the mirror 132.

Figure 5:
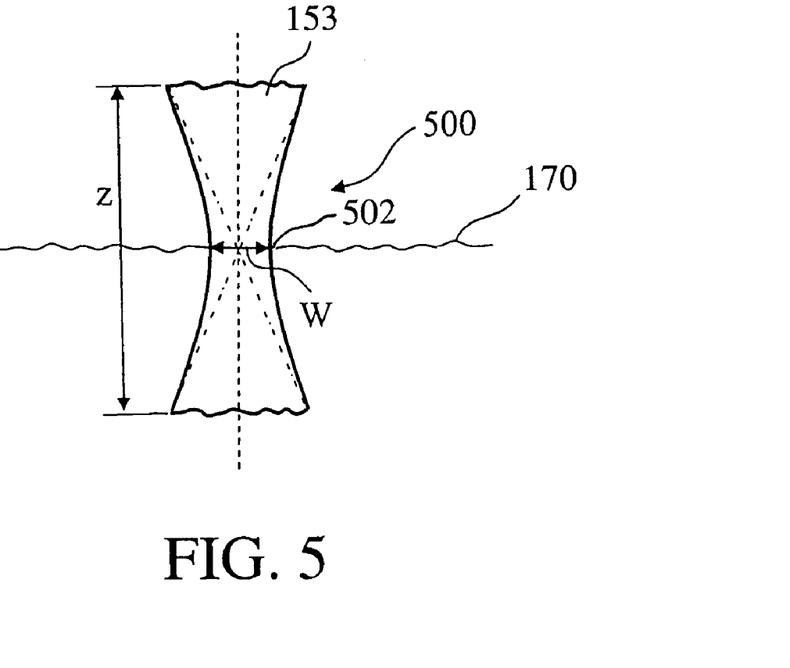
FIG. 5 shows an intensity distribution of the OCT-scanning beam in the OCT-scanning plane in the object region of the surgical microscope; and, FIG. 6 is a schematic showing the surgical microscope of FIG. 1 supplemented to show a mirror in the viewing path configured as a beam divider transmissive for the viewing beam path.

FIG. 5 shows the course of the intensity distribution of the OCT-scanning light beam 153 perpendicular to the OCT-scanning plane 170. In the OCT-scanning plane 170, the intensity distribution of the OCT-scanning radiation has a smallest constriction or waist 502. The diameter of the OCT-scanning beam path increases outside of the OCT-scanning plane. The OCT-scanning light beam 153 exits from the light conductor 151 of FIG. 4 with an approximately Gaussian-shaped beam profile. For this reason, the converging lens 157 and the microscope main objective 101 effect a so-called Gaussian bundle 500 of the OCT-scanning light beam 153 in the region of the OCT-scanning plane 170. This Gaussian bundle 500 is characterized by the confocal parameter (z) as an index for the longitudinal expansion of the waist of the Gaussian bundle and by the waist parameter W as an index for the diameter of the smallest constriction 502 of the OCT-scanning light beam 153, that is, for the diameter of the waist thereof. The following applies:

$$z = 2\frac{W^2 \pi}{\lambda},$$

wherein: $\lambda$ is the wavelength of the OCT-scanning light beam. The following relationship applies between the waist parameter W of the Gaussian bundle 500 and the waist parameter $W_0$ of the scanning light beam 153 (FIG. 4) which exits from the light conductor 151:

$$W = \beta W_0,$$

wherein: $\beta$ is the magnification parameter or demagnification parameter of the above-mentioned geometric image of the exit end of light conductor 151 of FIG. 1 in the OCT-scanning plane. The parameter $\beta$ is coupled to the focal length $f_1$ of the converging lens 157 of FIG. 1 and the focal length $f_2$ of the microscope main objective via the following relationship:

$$\frac{f_2}{f_1} = \beta$$

The size of structures, which can be resolved with the OCT-scanning light beam 153, is determined by the diameter of the beam 153 in the OCT-scanning plane 170, that is, by the waist parameter W. If, for example, an application requires a lateral resolution of the OCT-system in the surgical microscope of approximately 40 µm, then, according to the Nyquist theorem, the cross section of the OCT-scanning light beam 153 must amount to approximately 20 µm on the surface. For a given wavelength $\lambda$ for the OCT-scanning light beam 153 of FIG. 1, the magnification of the optical image in the OCT-beam path and the diameter of the fiber core in the light conductor 151 must be suitably selected for a desired resolution of the OCT-system 152.

The confocal parameter (z) as an index for the longitudinal expansion of the waist of the Gaussian bundle determines the axial depth of field from which backscattered light can be detected in the OCT-scanning beam path 153 of FIG. 1. The smaller the confocal parameter (z), the greater is the loss of the OCT-system with respect to lateral resolution when removing an object from the OCT-scanning plane 170 with this object having been scanned with the OCT-scanning beam. The reason for this is that the location of the scatter centers can be localized only within the "funnel" defined by the waist parameter W and the confocal parameter (z).

As the axial resolution of an OCT-system is delimited on the one hand by the specific coherence length of the light of the light source utilized in the OCT-system and, on the other hand, the lateral resolution of the OCT-system decreases when the depth index thereof exceeds the expansion given by the confocal parameter (z), then the adjustment of the confocal parameter (z) to the depth index of the OCT-system is favorable. The depth index is a measuring range within which scattering centers in the object can be measured in the z-direction.

For a specific wavelength $\lambda$ of the OCT-scanning light beam 153, the possible lateral resolution of the OCT-system of FIG. 1 results because the wavelength $\lambda$ and the confocal parameter (z) determine the waist parameter W. The optical units in the OCT-scanning beam path 153 of FIG. 1 and the dimensioning of the fiber core of the light conductor 151 are then to be selected so that the particular waist parameter W results.

The surgical microscope 100 is so designed that the focus plane 103 of the microscope main objective 101 for the visible spectral range and the OCT-scanning plane 170 are coincident. Then, the waist 502 of the OCT-scanning light beam shown in FIG. 5 lies in the focus plane of the surgical microscope.

Alternative to this design of the surgical microscope, an offset of the OCT-scanning plane and the focus plane of the surgical microscope can be provided. Preferably, this offset is not greater than the confocal parameter (z) of the OCT-scanning light beam in the region of the OCT-scanning plane. This makes it possible, for example, to visualize an object region utilizing OCT with this object region lying directly below the focus plane of the surgical microscope. However, it can also be purposeful to provide, for a specific application, a defined offset which exceeds the confocal parameter in order, for example, to examine the front side of the cornea of the eye of a patient with the surgical microscope and, at the same time, to visualize the rear side of the cornea of the patient eye or the lens thereof by means of the OCT-system.

The depth index for the OCT-system in the object region can be maximized in that the OCT-scanning plane is removed further from the microscope main objective 101 of FIG. 1 by the Rayleigh parameter (z).

A modified embodiment of the surgical microscope 100 as explained with respect to FIG. 1 contains a focusable microscope main objective having an adjustable focal length. This measure too makes possible the displacement of an OCT-scanning plane and the change of the geometric image of the light conductor exit end into the OCT-scanning plane.

Figure 6:
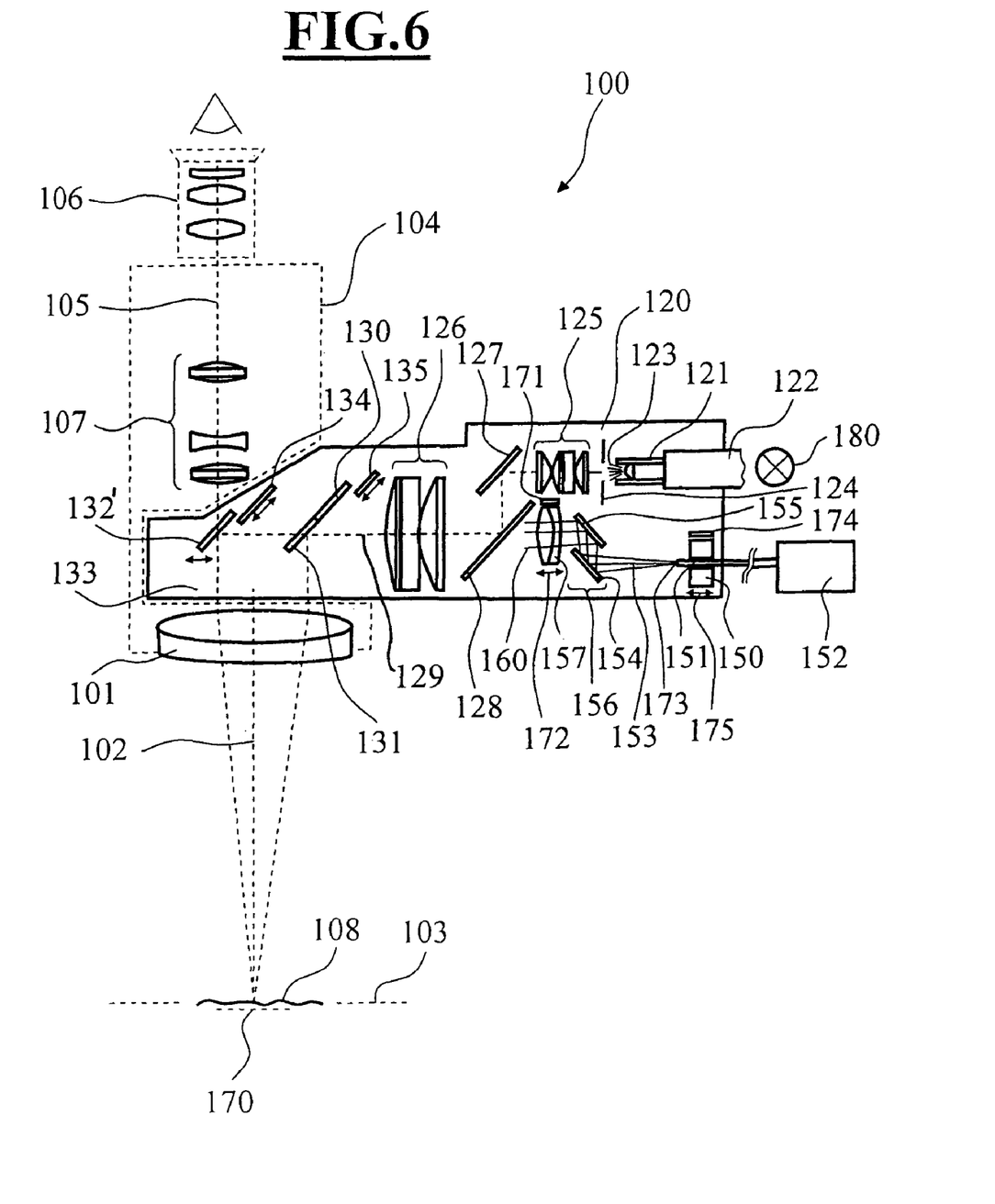

As shown in FIG. 6, a mirror 132' reflects light travelling along optical axis 129 and is a path-folding unit configured as a beam divider or beam splitter through which the viewing beam path 105 of the surgical microscope passes. In this way, the illuminating light is guided in the viewing beam path of the surgical microscope to the object region 108.

It is understood that the foregoing description is that of the preferred embodiments of the invention and that various changes and modifications may be made thereto without departing from the spirit and scope of the invention as defined in the appended claims.

What is claimed is:

1. A surgical microscope defining a viewing beam path for examining an object region, the surgical microscope comprising:
   an illuminating system defining an illuminating beam path and including a light source for generating an illuminating light;
   said illuminating system further including a field diaphragm arranged in said illuminating beam path and being illuminated by said illuminating light;
   said illuminating system further including an illuminating optic arranged in said illuminating beam path downstream of said field diaphragm for imaging said field diaphragm at infinity with an illuminating beam having parallel rays;
   said illuminating optic including first and second lens assemblies arranged in said illuminating beam path;
   an objective configured as a microscope main objective to permit the viewing beam to pass therethrough;
   said microscope main objective being arranged in said illuminating beam path for imaging said field diaphragm onto said object region;
   an OCT-system for examining said object region;
   said OCT-system providing an OCT-scanning beam guided through said microscope main objective;
   an in-coupling element disposed in said illuminating beam path between said first and second lens assemblies for coupling said OCT-scanning beam into said illuminating beam path so as to form a composite beam comprising said illuminating beam and said OCT-scanning beam passing through said second lens assembly and along said illuminating beam path;
   said microscope main objective having a side facing away from said object region; and,
   a path-folding unit mounted between said side of said microscope main objective and said second lens assembly for directing said composite beam to said microscope main objective.

2. The surgical microscope of claim 1, wherein said in-coupling element is a divider mirror.

3. The surgical microscope of claim 2, wherein said divider mirror is a planar mirror.

4. The surgical microscope of claim 1, wherein said in-coupling element is a divider cube.

5. The surgical microscope of claim 1, wherein said path-folding unit is configured as a beam splitter transmissive for said viewing beam path.

6. The surgical microscope of claim 1, wherein said OCT-system comprises a first scanning mirror for scanning said OCT-scanning beam; and, a first device for rotating said first scanning mirror about a first rotational axis.

7. The surgical microscope of claim 6, wherein said OCT-system further comprises a second scanning mirror for scanning said OCT-scanning beam; and, a second device for rotating said second scanning mirror about a second rotational axis laterally offset at a right angle to said first rotational axis.

8. The surgical microscope of claim 1, wherein said OCT-system further comprises: a light conductor having an end portion having a light exit end face for said OCT-scanning beam; and, means for moving said end portion.

9. The surgical microscope of claim 1, wherein said OCT-system comprises a collimating optic for coacting with said second lens assembly to transfer said OCT-scanning beam into an OCT-scanning beam having essentially parallel rays.

10. The surgical microscope of claim 9, wherein said collimating optic defines an OCT-scanning plane; and, said OCT-system further comprises means for moving said collimating optic to adjust said OCT-scanning plane.

11. An illuminating module for attachment to a surgical microscope defining a viewing beam path for examining an object region and the surgical microscope having a microscope main objective for passing a viewing beam along said viewing beam path to said object region, said microscope main objective having a side facing away from said object region, the illuminating module comprising:
   an illuminating system defining an illuminating beam path;
   a first receptacle for accommodating a first light conductor for providing illuminating light;
   said illuminating system further including: a field diaphragm arranged in said illuminating beam path and being illuminated by said illuminating light; and, an illuminating optic disposed in said illuminating beam path downstream of said field diaphragm for imaging said field diaphragm at infinity with an illuminating beam having parallel rays;
   said illuminating optic including first and second lens assemblies arranged in said illuminating beam path;
   a second receptacle for accommodating a second light conductor for providing an OCT-scanning beam of an OCT-system;
   an in-coupling element disposed in said illuminating beam path between said first and second lens assemblies for coupling said OCT-scanning beam into said illuminating beam path so as to form a composite beam comprising said illuminating beam and said OCT-scanning beam passing through said second lens assembly and along said illuminating beam path; and,
   a path-folding unit mounted between said side of said microscope main objective and said second lens assembly for directing said composite beam to said microscope main objective.

12. The illuminating module of claim 11, wherein said in-coupling element is a divider mirror.

13. The illuminating module of claim 12, wherein said divider mirror is a planar mirror.

14. The illuminating module of claim 11, wherein said in-coupling element is a divider cube.

15. The illuminating module of claim 11, further comprising a device scanning said OCT-scanning beam.

16. The illuminating module of claim 15, wherein said device for scanning said OCT-scanning beam comprises a first scanning mirror for scanning said OCT-scanning beam; and, a first device for rotating said first scanning mirror about a first rotational axis.

17. The illuminating module of claim 16, wherein said device for scanning said OCT-scanning beam further comprises a second scanning mirror for scanning said OCT-scanning beam; and, a second device for rotating said second scanning mirror about a second rotational axis laterally offset at a right angle to said first rotational axis.

18. The illuminating module of claim 11, wherein said second light conductor has an end portion having a light exit end face for said OCT-scanning beam; and, means for moving said end portion.

19. The illuminating module of claim 11, further comprising a collimating optic for coacting with said second lens assembly to transfer said OCT-scanning beam into an OCT-scanning beam having essentially parallel rays.

20. The illuminating module of claim 19, wherein said collimating optic defines an OCT-scanning plane; and, said OCT-system further comprises means for moving said collimating optic to adjust said OCT-scanning plane.

21. A compact illuminating and OCT-scanning module for attachment to a surgical microscope defining a viewing beam path for examining an object region and the surgical microscope having a microscope main objective for passing a viewing beam along said viewing beam path to said object region, said microscope main objective having a side facing away from said object region, the illuminating module comprising:
- an illuminating system generating an illuminating beam and defining an illuminating beam path;
- a first receptacle for accommodating a first light conductor for providing illuminating light for said illuminating beam;
- said illuminating system further including: a field diaphragm arranged in said illuminating beam path and being illuminated by said illuminating light; and, an illuminating optic disposed in said illuminating beam path downstream of said field diaphragm for imaging said field diaphragm at infinity with an illuminating beam having parallel rays;
- said illuminating optic including first and second lens assemblies arranged in said illuminating beam path;
- a second receptacle for accommodating a second light conductor for providing an OCT-scanning beam of an OCT-system;
- an OCT-scanning unit disposed downstream of said second light conductor for imparting a scanning movement to said OCT-scanning beam;
- an in-coupling element disposed downstream of said OCT-scanning unit and in said illuminating beam path between said first and second lens assemblies for coupling said OCT-scanning beam into said illuminating beam path so as to superpose said OCT-scanning beam onto said illuminating beam to form a composite beam passing through said second lens assembly and along said illuminating beam path; and,
- a path-folding unit mounted between said side of said microscope main objective and said second lens assembly for directing said composite beam to said microscope main objective.

22. The compact illuminating and OCT-scanning module of claim 21, wherein said OCT-scanning unit comprises a scanning mirror for scanning said OCT-scanning beam; and, a device for rotating said scanning mirror about a rotational axis.

23. The compact illuminating and OCT-scanning module of claim 21, further comprising said OCT-system mounted within said module.

* * * * *

UNITED STATES PATENT AND TRADEMARK OFFICE
CERTIFICATE OF CORRECTION

PATENT NO. : 7,889,423 B2  Page 1 of 1
APPLICATION NO. : 11/984817
DATED : February 15, 2011
INVENTOR(S) : Peter Reimer et al.

It is certified that error appears in the above-identified patent and that said Letters Patent is hereby corrected as shown below:

Title Page:
Under (30) Foreign Application Priority Data: delete
"Nov. 6, 2006 (DE) ............ 10 2006 052 513".

Signed and Sealed this
Thirty-first Day of May, 2011

David J. Kappos
*Director of the United States Patent and Trademark Office*